US009801716B2

United States Patent
Pollack et al.

(10) Patent No.: US 9,801,716 B2
(45) Date of Patent: Oct. 31, 2017

(54) SYSTEM AND METHOD FOR PLACING A PROSTHETIC AORTIC VALVE

(71) Applicants: Jordan Pollack, Ann Arbor, MI (US); Theodore French, III, Rocky River, OH (US); Kenny Tang, Staten Island, NY (US); Andrew Kalenkiewicz, Monroe, MI (US)

(72) Inventors: Jordan Pollack, Ann Arbor, MI (US); Theodore French, III, Rocky River, OH (US); Kenny Tang, Staten Island, NY (US); Andrew Kalenkiewicz, Monroe, MI (US)

(73) Assignee: Lifesavr Solutions LLC, Minneapolis, MN (US)

( * ) Notice: Subject to any disclaimer, the term of this patent is extended or adjusted under 35 U.S.C. 154(b) by 186 days.

(21) Appl. No.: 14/713,790

(22) Filed: May 15, 2015

(65) Prior Publication Data

US 2015/0327997 A1 Nov. 19, 2015

Related U.S. Application Data

(60) Provisional application No. 61/994,678, filed on May 16, 2014.

(51) Int. Cl.
| | |
|---|---|
| *A61F 2/06* | (2013.01) |
| *A61F 2/24* | (2006.01) |
| *A61B 34/20* | (2016.01) |
| *A61B 90/00* | (2016.01) |
| *A61B 34/00* | (2016.01) |
| *A61B 17/00* | (2006.01) |
| *A61B 17/22* | (2006.01) |

(52) U.S. Cl.
CPC ............ *A61F 2/2427* (2013.01); *A61B 34/20* (2016.02); *A61B 34/25* (2016.02); *A61B 90/00* (2016.02); *A61B 90/37* (2016.02); *A61B 2017/00703* (2013.01); *A61B 2017/22042* (2013.01); *A61B 2034/256* (2016.02); *A61B 2090/065* (2016.02)

(58) Field of Classification Search
CPC ................... A61F 2/2427; A61F 2/966; A61F 2002/9517; A61F 2/2436; A61F 2/95; A61F 2/2466; A61B 2017/00703; A61B 2017/22042; A61B 2034/256; A61B 2090/065; A61B 34/20; A61B 34/25; A61B 90/00; A61B 90/37; A61B 2017/00243
USPC .............................................. 623/1.11, 2.11
See application file for complete search history.

(56) References Cited

U.S. PATENT DOCUMENTS

| | | | |
|---|---|---|---|
| 2007/0060998 A1* | 3/2007 | Butterwick | A61F 2/064 623/1.11 |
| 2008/0139915 A1* | 6/2008 | Dolan | A61B 5/06 600/407 |
| 2010/0268067 A1* | 10/2010 | Razzaque | A61B 8/4245 600/424 |
| 2014/0155822 A1* | 6/2014 | Buckner | A61M 25/0105 604/95.04 |

* cited by examiner

*Primary Examiner* — Katherine M Shi
(74) *Attorney, Agent, or Firm* — Jay Schloff; Aidenbaum Schloff and Bloom PLLC (57) ABSTRACT

A system and method including a guide wire having a plurality of sensors attached near an end of the guide wire, and a processor configured to determine a position of a body component and a position of a catheter moving along the guide wire based on the signals received from the plurality of sensors. Feedback information can be generated based on these determined positions to help guide a medical procedure.

7 Claims, 6 Drawing Sheets

SYSTEM AND METHOD FOR PLACING A PROSTHETIC AORTIC VALVE

CROSS-REFERENCE TO RELATED APPLICATIONS

The present application claims priority under 35 U.S.C. §119 under U.S. Provisional Patent Application Ser. No. 61/994,678, filed on May 16, 2014, the disclosure of which is incorporated by reference.

FIELD OF THE DISCLOSURE

The present disclosure relates to the placing of a prosthetic aortic valve in a human patient, and more particularly, to a system and method of placing a prosthetic aortic valve in a human patient by way of a guide wire and catheter having a plurality of sensors in communication with a processor.

BACKGROUND

Aortic stenosis is a disease that affects over sixteen million individuals over the age of sixty-five in the United States alone, and is characterized by a narrowing of the aortic valve in the heart, resulting in an obstruction to normal blood flow. In normal operation, leaflets of the aortic valve allow or restrict blood flow based on their respective open and closed states. That is, and generally, in such open state, the leaflets of a healthy aortic valve open wide, and in such closed state, the leaflets of a healthy aortic valve close at least substantially completely along with the beating of a person's heart. Contrastingly, the leaflets of a diseased, open aortic valve do not open as wide as those of a healthy, open aortic valve, and the leaflets of the diseased, closed aortic valve may not close sufficiently. A diseased aortic valve thus obstructs blood flow and poses significant health risks.

The standard treatment for severe aortic stenosis is open-heart surgery to replace the effected aortic valve with a prosthetic, mechanical valve. However, this procedure is not an option for high-risk, inoperable patients, and so alternative treatments often must be considered. The primary alternative to the aforesaid open-heart surgical procedure is transcatheter aortic valve replacement (commonly and hereinafter referred to as "TAVR"), a minimally invasive procedure that delivers a prosthetic valve through the patient's arteries, thereby obviating the opening of the patient's chest. In a typical TAVR procedure, a relatively small incision is made in the patient's groin in order to give the doctor access to a major artery that leads to the aorta. The physician thereafter inserts a guide wire within the incision to send a catheter and a replacement, prosthetic aortic valve through the aorta to the patient's heart. To position this replacement valve, physicians generally use florescent dye with real time fluoroscopy in conjunction with an ultrasound probe placed in the patient's esophagus.

Using known TAVR positioning technologies, physicians rely on two-dimensional imagery to determine the correct position at which to place the prosthetic aortic valve. While somewhat effective, this method introduces a degree of uncertainty in the replacement valve positioning procedure, which results in a misplacement rate of as much as ten percent (according to the PARTNER II Clinical Trials). Aortic valve misplacement, in turn, often results in significant paravalvular leak (i.e., leakage of blood around such valve), thereby necessitating the placement of a second such valve within the first such replacement valve. Furthermore, not only is it estimated that up to ten percent of prosthetic valves are misplaced through TAVR procedures, but it is also estimated that two and a half percent of all TAVR procedures require revision. The placement of a second valve results in additional radiation exposure, contrast dye exposure, and anesthesia exposure, each of which individually and in combination creates an increased risk for further health complications, such as kidney damage or failure.

Thus, while existing alternatives to open-heart surgery exist for treating aortic stenosis, various drawbacks, including those mentioned above, remain. Consequently, there exists a need to position a prosthetic valve quickly, accurately, and without revision, and, towards that end, there exists a need for technology that provides physicians with a more accurate, quantitative method for determining the correct position at which to deploy or place a prosthetic aortic valve during a TAVR procedure.

SUMMARY OF THE INVENTION

In view of the foregoing disadvantages of the prior art, disclosed herein are improved catheter guide wires and a catheter guide wire system that provides positioning feedback.

In an embodiment, a system for placing a prosthetic aortic valve includes a guide wire having at least one sensor coupled to a distal end thereof and a processor in communication with the at least one sensor and configured to execute computer-readable instructions to determine the positions of a heart valve and a catheter. The processor uses signals received from the sensor(s) to determine the location of the patient's native aortic valve and the location of a catheter-fed prosthetic aortic valve in order to properly place same. Based on the determined location of the aortic valve and the catheter, the system may provide location-based feedback to a physician performing the operation, and the physician may use the feedback to accurately position the prosthetic valve within the patient.

In another embodiment, a method for placing a prosthetic aortic valve comprises the steps of: (i) inserting a guide wire through a vasculature; (ii) detecting, by at least one sensor disposed on the guide wire, a body component of a patient; (iii) determining, by way of a processor in communication with the at least one sensor, a position of the body component based on one or more signals received from the sensor(s); (iv) feeding a catheter along the guide wire through the vasculature; (v) detecting, by the sensor(s), the catheter and the valve enclosed within the catheter as the catheter is fed along the guide wire; (vi) determining, by a processor in communication with the sensor(s), a position of the catheter along the guide wire based on one or more signals received from the sensor(s); and (vii) generating, by the processor, feedback information indicating the position of the catheter relative to the position of the subject body component.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific objects attained by its uses, reference should be made to the accompanying drawings and detailed description in which there are illustrated and described exemplary embodiments of the present disclosure.

DESCRIPTION OF THE DRAWINGS

The advantages and features of the present invention will become better understood with reference to the following

Like reference numerals refer to like parts throughout the description of several views of the drawings.

DETAILED DESCRIPTION OF THE DISCLOSURE

The best mode for carrying out the present disclosure is presented in terms of its preferred embodiments, herein depicted in the accompanying figures. The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The terms "a" and "an" herein do not denote a limitation of quantity, but rather denote the presence of at least one of the referenced items.

Figure 1:
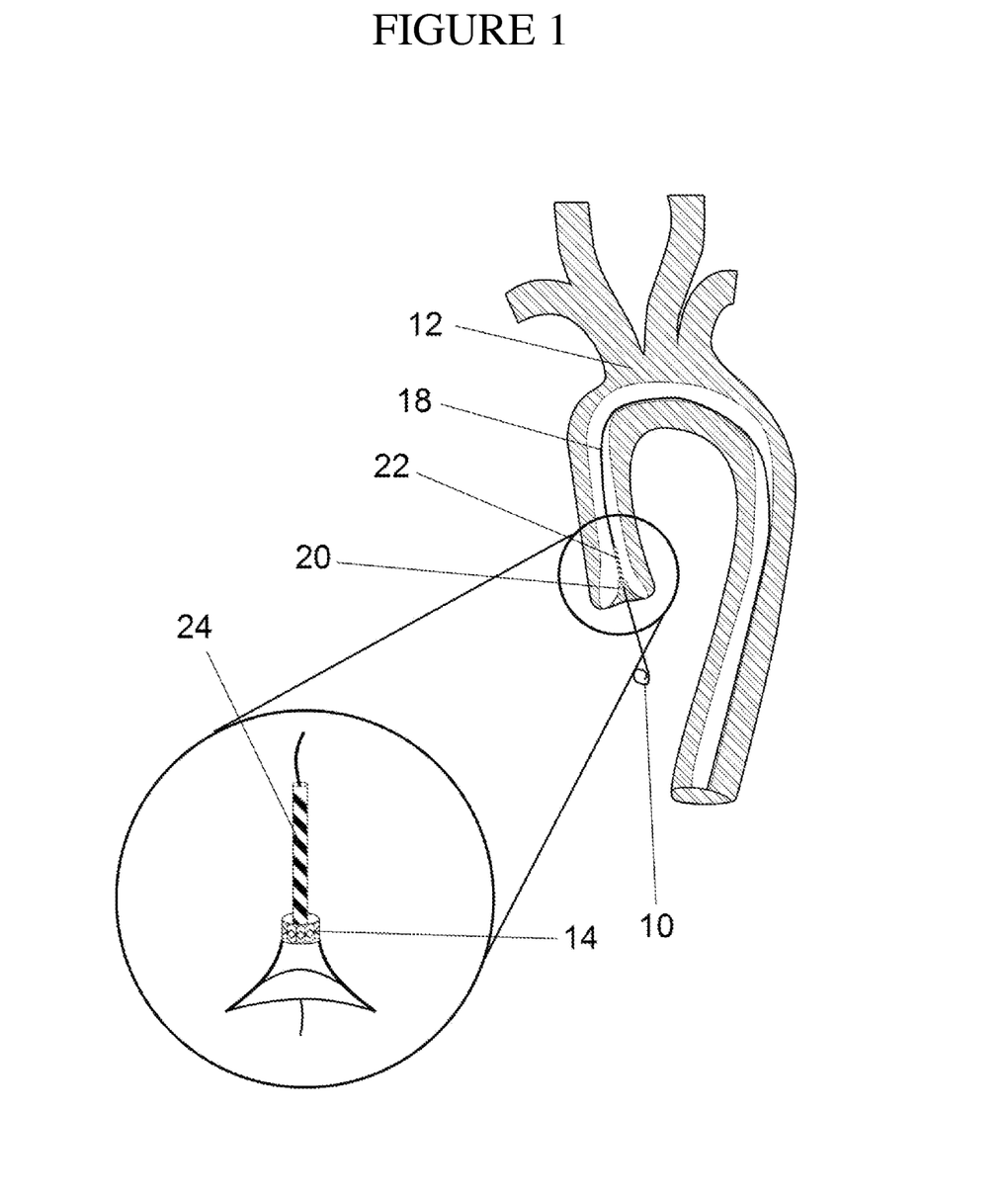
FIG. 1 shows an exemplary depiction of the disclosed guide wire system for placing a prosthetic aortic valve in accordance with an exemplary embodiment of the present disclosure.

Referring to the accompanying drawings in which like reference numbers indicate like elements, a guide wire 10 is shown in FIG. 1 as extending through a patient's aorta 12, as part of the TAVR procedure. As is known in the art, the TAVR procedure is performed for the placement of a prosthetic aortic valve 14 that, upon successful installation and proper operation, gives a patient healthy blood flow through the aorta 12. In a traditional TAVR operation, the guide wire 10 extends through the patient's femoral artery (not illustrated), into the patient's aorta 12, and into the patient's heart (not illustrated). After the guide wire 10 has been moved into a desired position, the guide wire 10 remains in place and a catheter 18 slides over the guide wire 10 towards the diseased heart valve 20. To keep the guide wire 10 in place, the guide wire 10 may be clipped to a stationary or other object before guiding the catheter 18. The catheter 18 is slipped over the guide wire 10, and a physician thereafter pushes the catheter 18 up the aorta 12 toward the diseased heart valve 20 along the guide wire 10 using a medical tool. The catheter 18 opens the patient's diseased heart valve 20, and, through use of the catheter 18, the physician is able to deploy or place a prosthetic aortic valve 14. Once the physician so properly positions such replacement, prosthetic aortic valve 14, the guide wire 10 and catheter 18 are removed from the patient's body, and the diseased heart valve 20 is thus replaced by the fully-functioning, prosthetic aortic valve 14.

In a preferred embodiment, the guide wire 10 has a set of sensors 22 coupled to and disposed near a distal end of the guide wire 10. As explained in greater detail below, the sensors 22 provide positioning feedback to the physician performing the replacement procedure, thereby assisting the physician in accurately placing the prosthetic aortic valve 14. The sensors 22 are in communication with a processor (not shown) that operates on and processes information derived from the sensors 22 and are capable of determining the locations and positions of the aortic valve 20 and the catheter 18 as same moves along the guide wire 10. The aortic valve 20 may generally only be three to four millimeters in depth (measured from the apex of the leaflets thereof to the center annulus thereof), so the physician performing the TAVR procedure has very little margin of error for placement of the prosthetic aortic valve 14. The sensors 22 may provide the doctor with very accurate and, over many uses, precise measurements such that the doctor is able to place the prosthetic aortic valve 1 within an error tolerance of two millimeters or lower, depending on the size of the sensors 22.

In an embodiment, the sensors 22 may wrap around, extend along, or otherwise couple to a length of approximately ten centimeters of the guide wire 10 to create a functional zone of sensors 24. The functional zone of sensors 24 should be placed at or near the distal end of the guide wire 10 such that a portion of the functional zone extends into the patient's heart when the guide wire 10 has been moved into the appropriate position inside the patient. The number of sensors 22 in the functional zone may depend on a number of factors such as a designated size for each sensor 22 and an acceptable cost range for the guide wire 10. Cost considerations may also impact the size of the sensors 22. The smaller each sensor 22 is, the more accurately a physician may place the prosthetic aortic valve 14. However, as the sensors 22 decrease in size, the number of sensors 22 rises, and the cost to manufacture each guide wire 10 rises. Because the guide wire 10 and the sensors 22 enter a patient's body, neither the guide wire 10 nor the sensors 22 may be reused. Because each TAVR procedure requires a new guide wire 10 having new sensors 22, costs to the hospital, the patient, and/or the insurance company may become an important consideration. The length of the functional zone, which is directly related to the size of the sensors 22 and the number of sensors 22, may also depend on cost implications. To illustrate this point, and in an exemplary embodiment, the number of sensors 22 may be any number from 10 to 500 sensors, and the size of the sensors 22 may range from around 100 microns to around 1 millimeter (e.g., 100 microns, 200 microns, 500 microns, or 1 mm).

The length of the functional zone should be relatively short so as not to contact the aortic arch during final placement of the guide wire 10. As shown in FIG. 1, the aorta 12 first extends upward (if a person is standing) from the heart, and after a short distance (roughly five to ten centimeters, depending on and as varies by the person) the aorta 12 may begin to curve downward towards a person's torso and legs. The sensors 22 may bend or create false positives if contacting the aortic arch during final placement of the guide wire 10. FIG. 1 also illustrates the proper length and placement of the functional zone in the patient. As shown therein, the functional zone extends at least partially into the heart past the aortic valve 20 and ends before the aortic arch.

Figure 2:
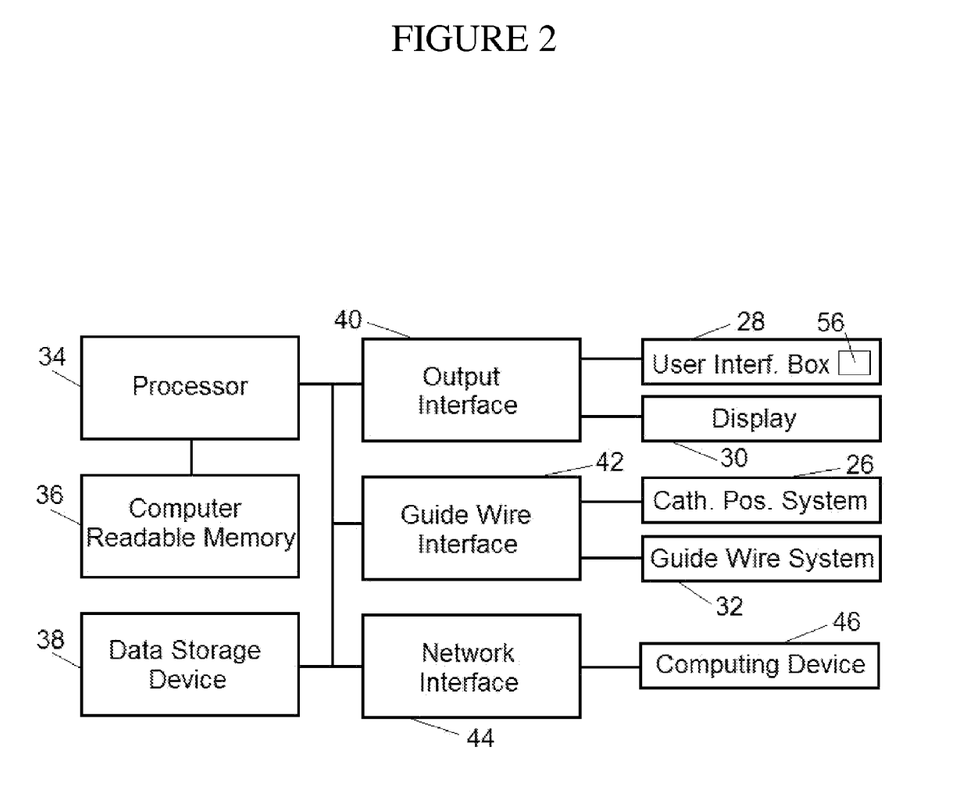
FIG. 2 shows an exemplary block diagram for the disclosed catheter positioning system in accordance with an exemplary embodiment of the present disclosure.

FIG. 2 illustrates an exemplary block diagram for the catheter positioning system 26. The catheter positioning system 26 comprises a user interface box 28, a display 30, and the guide wire system 32. The user interface box 28 may include a processor 34, computer readable memory 36, a data storage device 38, an output interface 40, and a guide wire interface 42. The user interface box 28 may also include a network interface 44.

The processor 34 may execute software instructions included in a software application stored in the computer readable memory 36. For example, the processor 34 may process data received from the sensors 22, determine the location of the prosthetic aortic valve and the catheter and provide feedback data to a physician through the display 30. The processor 34 may communicate with all the other components of the user interface box 28 through a connection, such as through one or more system buses.

The data storage device 38 may comprise a solid state hard drive, a hard disk drive, a collection of flash memory, or any other long-term data storage device. The data storage device 38 may store data necessary for the surgery. For example, the data storage device 38 may store patient medical records about a patient undergoing a TAVR procedure. The patient medical records may be displayed to the physician to notify the physician about any allergies the patient may have, or any other medical information a physician may need during the TAVR procedure. The data storage device 38 may store information about the catheter, such as manufacturer specific dimensions of a manufacturer's catheter and prosthetic aortic valve. The data storage device 38 may also record readings from the sensors, such as the size of the patient's aortic valve. Saved information about the patient's aortic valve may be useful if the prosthetic aortic valve ever needs to be replaced. The data storage device 38 will also be capable of saving patient data related to computed tomography scans (said data hereinafter referred to as "CT scan data" and said scanning device hereinafter referred to as a "CT scanner"). The CT scan data is useful for knowing information about the dimensions of the patients aortic valve prior to the TAVR procedure. It can also assist the device with knowing the patients dimensions in order to find and properly align the prosthetic aortic valve.

The output interface 40 may be any interface used to display information to the physician during the TAVR procedure. The output interface 40 may display sensor data or feedback information to the physician that the physician may use to accurately place the prosthetic aortic valve. The output interface 40 may be a graphical processing unit, or the output interface 40 may be simply to connect to numeric screens that display sensor readings to the physician. The output interface 40 may further connect to a computing device 46 to upload sensor readings to a computer application running on the computing device 46. If the user interface box 28 may connect to a computing device 46, the output interface 40 may further comprise a universal serial bus interface.

The guide wire interface 42 may be an interface that receives signals from the sensors. The sensors may connect to the guide wire interface 42 through conductors 48 (see FIG. 1) extending along the guide wire. For example, the conductors 48 may take the form of a series of wires. Such wires may be coiled around the guide wire to the guide wire interface 42. Depending on the number of sensors, the guide wire interface 42 may use a similar numbered pin connector. For example, if the guide wire includes ten sensors, the guide wire interface 42 may connect to the sensors through a ten-pin connector. More pins may be added if necessary for ground wires or signals indicating that data is ready to be received. The guide wire interface 42 may include a multiplexer that cycles through the connected sensors so that the sensor signals may be received by the processor 34 one at a time. The guide wire interface 42 may receive analog signals from the sensors, and the guide wire interface 42 may convert those analog signals into a digital signal usable by the processor 34 using an analog-to-digital converter.

The network interface 44 may include any wired or wireless network connection, including without limitation Bluetooth®, 802.11, or a cellular connection. The processor 34 may use the network interface 44 to download software application program updates, download patient medical records, receive data from a CT scanner, or transmit data about the TAVR procedure to another network-enabled computing device 46. The network interface 44 may be an optional component of the user interface box 28.

Figure 3:
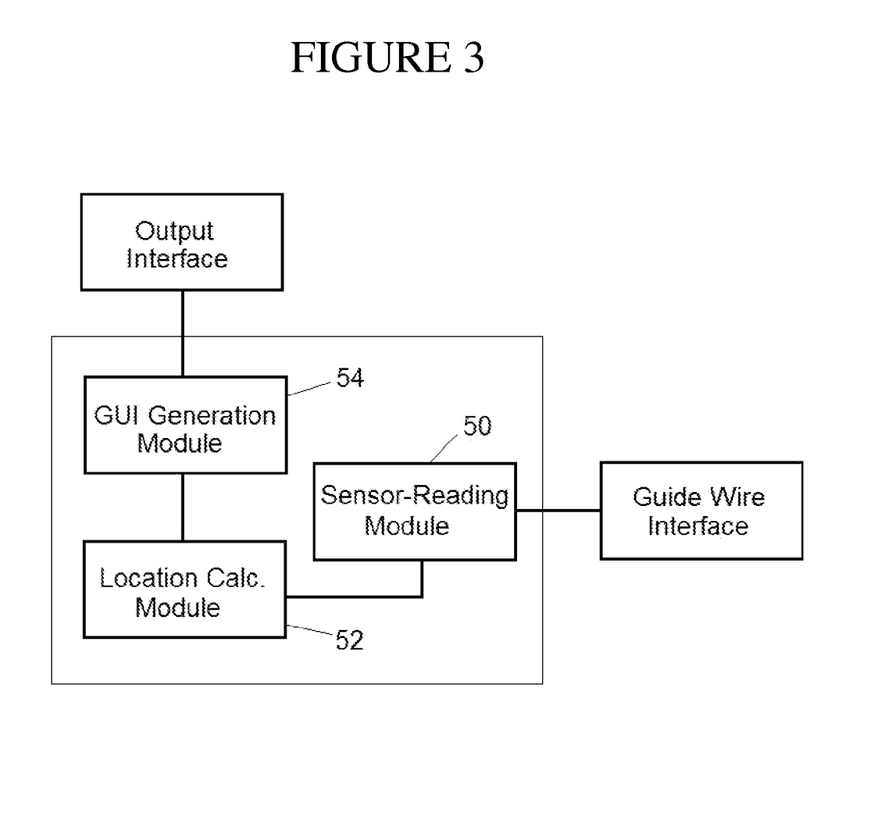
FIG. 3 shows an exemplary block diagram for a software system operating in connection with the disclosed guide wire system in accordance with an exemplary embodiment of the present disclosure.

FIG. 3 depicts an exemplary software application for an exemplary embodiment. The software application preferably comprises a plurality of computer-executable instructions resident on a non-transitory computer-readable storage medium such as the computer readable memory. The instructions may include instructions defining various modules such as a sensor reading module 50, a location-calculating module 52, and a user interface (hereinafter referred to exemplarily as "GUI," it being understood that the user interface in one or more exemplary embodiments may not feature graphical representations) generation module 54.

The sensor-reading module 50 may receive sensor signals from the sensors through the guide wire interface. The sensor-reading module 50 may interpret the signals from the sensors. For example, the sensor reading module 50 may attach metadata to the sensor signals so that the processor and the location calculating module 52 may know which sensor provided each sensor reading.

The location-calculating module 52 receives the data from the sensor-reading module 50 and uses the sensor readings to determine the location of the native aortic valve and the catheter, which includes the prosthetic aortic valve coupled to a portion thereof. The location of the prosthetic aortic valve may be a location along the guide wire (i.e. the aortic valve contacts sensor number X, X and Y, or any other way of indicating which sensors contact the aortic valve). The location-calculating module 52 may determine the location of the aortic valve by determining a sensor where sensors are impacted not constantly, but periodically, like the beating of the heart. As described above, the aortic valve opens and closes with the beating of the heart, so the aortic valve also exhibits a "heart beat" pattern that can be sensed by the sensors if the sensors are sufficiently proximate to the aortic valve. For example, when the sensors are co-located with the aortic valve, the aortic valve will contact the sensors as the heart beats. Thus, the location calculating module 52 can search for a periodic heartbeat-like signal coming from one or more of the received sensor signals. In a preferred embodiment, the sensors are strain sensors that produce a voltage when contacted, wherein the location-calculating module 52 can receive a voltage from the contacted sensors and thus record that location for alignment. The location-calculating module 52 searches for a voltage readout above a threshold value that is not a baseline measurement and may recalibrate as necessary to maintain an even such baseline measurement.

By searching for a heartbeat reading, the location-calculating module 52 may disregard false positives, such as if the sensors contact the aortic arch during insertion because the sensors may emit a constant voltage when contacted by the aortic arch until the sensors do not contact the aortic arch. After the aortic valve is found, the location-calculating module 52 may store its position along the sensors in the computer readable memory. This position information for the aortic valve can later be used by the processor during prosthetic aortic valve placement to facilitate a determination as to where the prosthetic aortic valve should be positioned. It should be understood that when the catheter is used for delivery of the prosthetic aortic valve, once the catheter opens, the catheter will mask the beating of the patient's aortic valve. Thus, after the catheter opens, the location-calculating module 52 cannot find the aortic valve and will need to reference the stored position data for aortic valve.

During insertion, the catheter will slide over the guide wire and sensors. As the catheter slides over the sensors, the sensors will produce a relatively constant signal, and the location-calculating module 52 can thus determine the location of the catheter based on which sensors provide the constant signal. For example, the location-calculating module 52 can track catheter movement by searching for a continuous contact signal that moves from the most proximal sensor (i.e., the sensor closest to the user interface box) toward the most distal sensor (i.e., the sensor furthest from the user interface box). Using the catheter position determination and the stored position for the aortic valve, the location-calculating module 52 may determine whether the catheter overlaps the saved position of the patient's aortic valve. Finally, as explained in greater detail below, the location-calculating module 52 may also perform more precise calculations to determine a location of the annulus of the aortic valve and a location of the annulus of the replacement, prosthetic aortic valve. During placement, it is desired that both the annulus of the aortic valve and the annulus of the prosthetic aortic valve overlap.

The GUI generation module 54 receives data from the location-calculating module 52 and displays the location of both the aortic valve and the catheter, provided that the catheter has been sensed by the sensors. In an embodiment, the GUI generation module 54 may present the information graphically or numerically depending on the display connected to the user interface box and the graphical processing power of the output interface. The GUI generation module 54 may display location data and also feedback data about whether the catheter is within an acceptable range for prosthetic valve placement. For example, the GUI generation module 54 may display a distance between the annulus of the prosthetic aortic valve and the position of the patient's native aortic valve, or the GUI generation module 54 may display a 3-D rendering of the patient's aorta, the aortic valve, and the movement of the catheter using sensor information in combination with other imaging devices, such as a CT scanner. While illustrated as separate components in FIG. 2, in some embodiments, the display 30 is integrated into the user interface box 28.

It is understood and contemplated that the software application may include features beyond those described above and/or shown in FIG. 3. For example, the software application may include a CT scan module that receives data from a CT scanner, such as through another interface or through the network interface. The CT scan module may analyze data from the CT scanner and use the additional CT scan data to verify that the data from the sensors is correct. The location-calculating module 52 may further use the CT scan data to make more precise location calculations.

The software application may also account for manufacturer-specific dimensions of a prosthetic aortic valve. The sizes and dimensions of each manufacturer's prosthetic aortic valve may vary, and by taking into account the sizes and dimensions of each manufacturer's prosthetic aortic valve, the software application may more accurately calculate a location of the annulus of each manufacturer's prosthetic aortic valve. The manufacturer-specific data may be stored in the data storage device and updated periodically with new manufacturer dimensions or products using the network interface.

The user interface box 28 diagrammed in FIG. 2 may include the display 30, which can be seen from the outside of the user interface box 28. The guide wire extends from the user interface box 28, and a coil of wires electrically connects the sensors to the user interface box 28. The user interface box 28 further receives power from a power source 56 connected to a power supply within the user interface box 28.

Figure 4A:
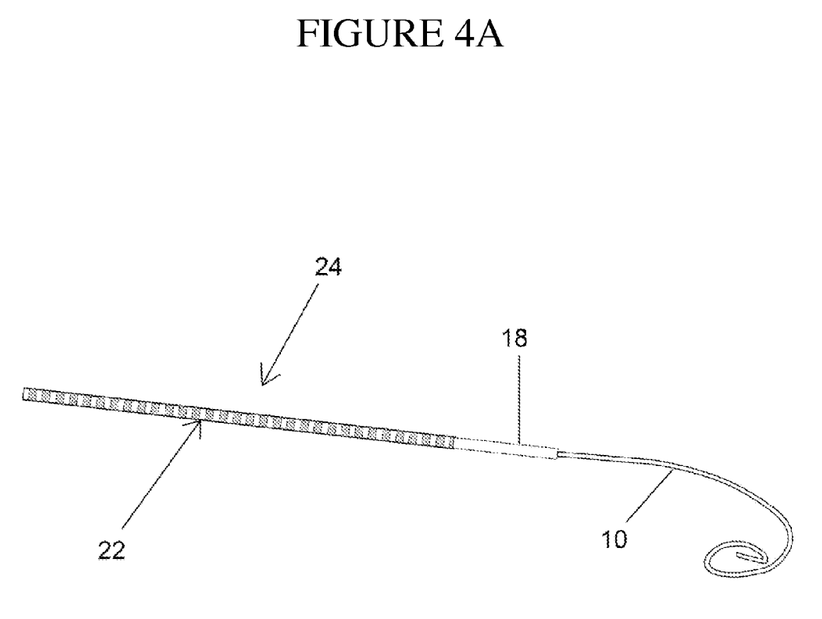
FIG. 4A shows a first exemplary depiction of the sensors arranged on the disclosed guide wire system in accordance with an exemplary embodiment of the present disclosure.
Figure 4B:
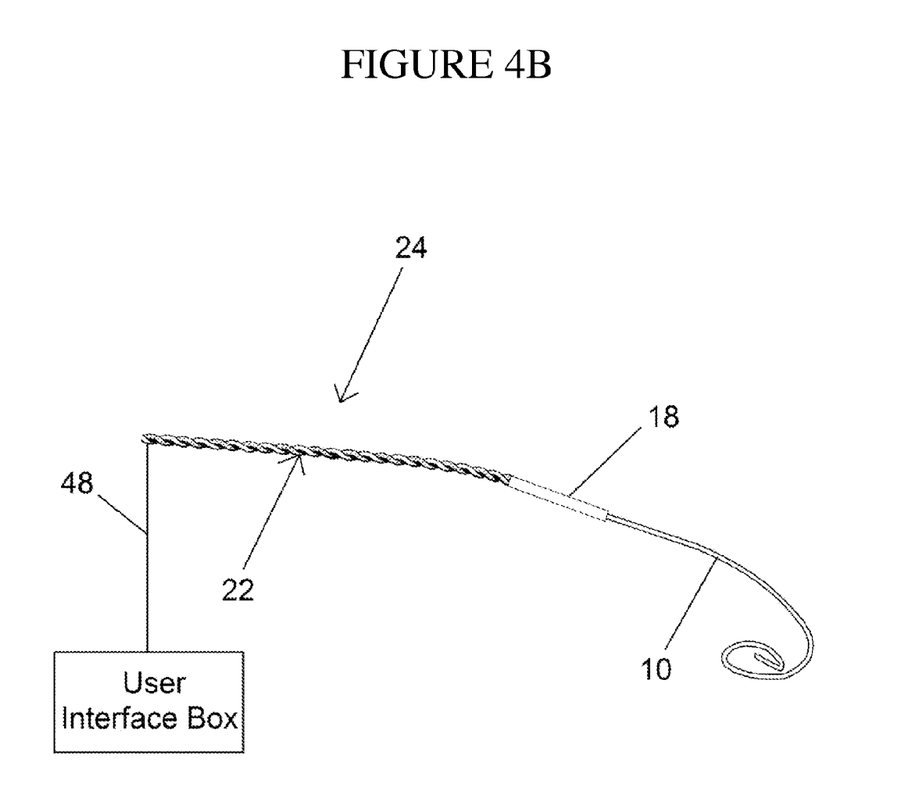
FIG. 4B shows a second exemplary depiction of the sensors arranged on the disclosed guide wire system in accordance with an exemplary embodiment of the present disclosure.

As stated above, and as shown in FIG. 1, the sensors 22 may connect to the user interface box (not shown) through a plurality of conductors 48, which, in an embodiment, are wires. In a preferred embodiment, the coupling of the sensors 22 to the guide wire 10 is supported by a quantity of silicone elastomer for insulation and adhesion to a stainless steel core. Each sensor 22 may wrap preferably one time around the guide wire 10 such that the sensors 22 create a stack. The sensors 22 may be annular in shape to fit around the guide wire 10. Notwithstanding anything to the contrary, it will be apparent that the sensors 22 generally must be independently or separately wired in order to effectively differentiate between them. FIG. 4A illustrates the stack of sensors 22. The dark and light bands of FIG. 4A each illustrate the sensors 22. The differing colors are shown for illustration purposes to illustrate a stack. As shown in FIG. 4A, a plurality of sensors 22 extend along the guide wire 10 in the functional zone 24. FIG. 4B illustrates another example of the sensors 22 extending along the guide wire 10. FIG. 4B also illustrates the coil of wires 48 connecting the sensors 22 to the user interface box.

Figure 5:
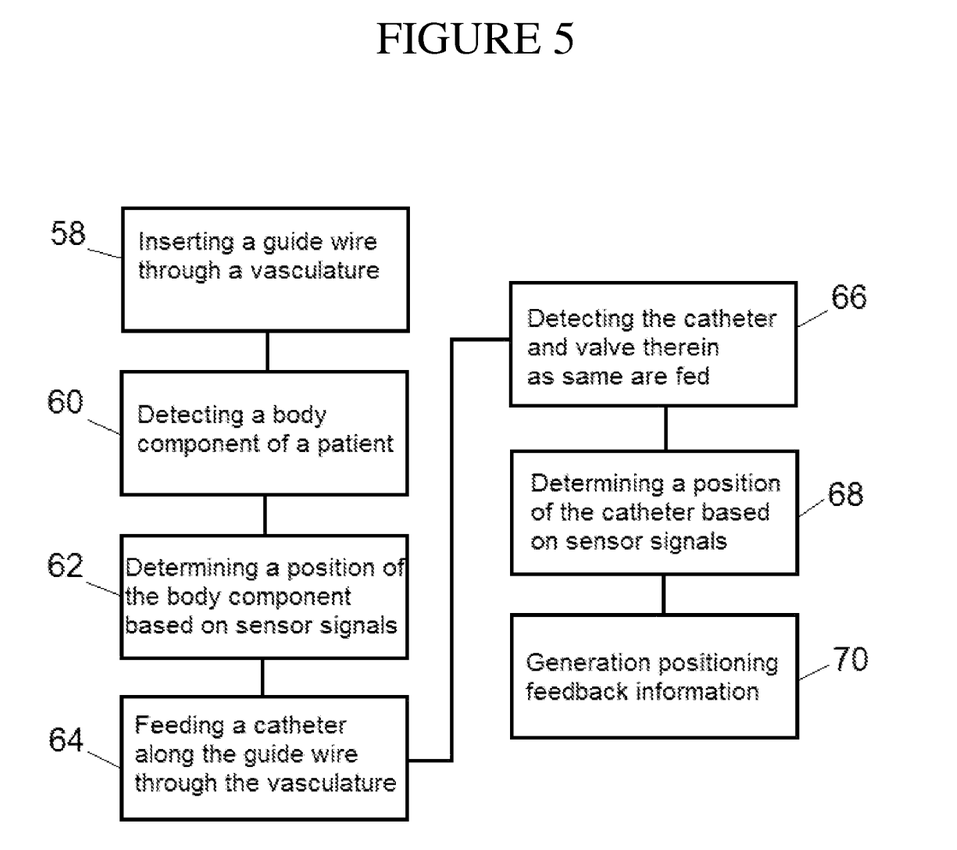
FIG. 5 shows an exemplary block diagram depiction of the disclosed method for operating a guide wire system and placing a prosthetic aortic valve in accordance with an exemplary embodiment of the present disclosure.

FIG. 5 illustrates a method for properly placing a prosthetic aortic valve during a TAVR operation, which method comprises the steps of inserting 58 a guide wire through a vasculature; detecting 60, by at least one sensor disposed on the guide wire, a body component of a patient; determining 62, by way of a processor in communication with the at least one sensor, a position of the body component based on one or more signals received from the at least one sensor; feeding 64 a catheter along the guide wire through the vasculature; detecting 66, by the at least one sensor, the catheter and the valve enclosed within the catheter as the catheter is fed along the guide wire; determining 68, by a processor in communication with the at least one sensor, a position of the catheter along the guide wire based on one or more signals received from the sensor; and generating 70, by the processor, feedback information indicating the position of the catheter relative to the position of the subject body component. The method begins when a physician inserts the guide wire into the patient's body and through the aorta. The physician feeds the guide wire through the patient's body until the distal end of the guide wire enters the patient's left ventricle. When the guide wire extends into the left ventricle, the patient's aortic valve will contact the functional zone of sensors. To ensure that the guide wire does not move, the physician may clip the wire near the proximate end of the guide wire where the guide wire enters the patient's body. Next 60, the aortic valve will contact the sensors with the beating of the patient's heart, and the location-calculating module analyzes sensor data to find the heartbeat-like sensor signals and determine the position of the aortic valve. More specifically, the location-calculating module determines the location of the coaptation point of the aortic valve (i.e., the point of contact with the leaflets thereof). The location-calculating module may determine a position of the annulus by determining the sensor that is closest to the user interface box and emits a heartbeat-like signal. While closing, the leaflets of the aortic valve are not flat, but they protrude up the aorta approximately three to four centimeters. In this way, the aortic valve forms a cone-like shape while closing. So, the sensor closest to the user interface box that still receives a heartbeat-like signal detects the location of the aortic valve's coaptation point, which location may thereafter be used to calculate the distance between the coaptation point and the annulus of the aortic valve and thus determine the location of said annulus; provided, however, that a correction of up to three to four centimeters may be necessary (depending on the patient) to properly determine the location of the aortic valve's annulus. As previously discussed, the position of the aortic valve is determined before expanding the catheter because the sensors will not be able to sense the patient's aortic valve after the catheter expands because the catheter blocks the patient's aortic valve. Calculating the location of the prosthetic valve's annulus may involve referencing dimension data about the prosthetic aortic valve from the data storage device, and the dimension data may be manufacturer specific.

The user interface box may display feedback information to the physician in the following portion of the method. The feedback information may include data indicating the determined location of the patient's aortic valve, data indicating the determined location of the catheter, data indicating the determined location of the prosthetic aortic valve's annulus, a determined distance between the annulus of the patient's aortic valve and the annulus of the prosthetic aortic valve, and/or directions to the doctor on whether to continue feeding the catheter along the guide wire or to pull the catheter backwards along the guide wire. The user interface box may provide any information that assists the doctor in locating a proper position for the prosthetic aortic valve.

Thus, it should be understood that the disclosure herein provided sets forth valuable positioning feedback information to physicians who perform TAVR procedures. While the exemplary embodiments have been described specifically for the TAVR procedure, it should be understood that the technology described herein may be useful in other medical procedures using guide wires. As such, the exemplary embodiments should not be limited to only TAVR applications The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

1. A system for placing a prosthetic aortic valve comprising:
    a guide wire capable of being at least partially inserted into a patient, said guide wire comprising a proximate end and a distal end, said distal end being the end at least partially inserted into a patient;
    a prosthetic device removably coupled to said guide wire, said prosthetic device capable of being received within the patient;
    at least one sensor disposed along at least a portion of said guide wire disposed at or near said distal end of said guide wire; and
    a processor,
    wherein said at least one sensor is configured to detect contact with a body component of the patient and produce a signal relative to such contact, and
    wherein said processor is configured to receive and interpret at least one signal produced by said at least one sensor and thereby determine based on said at least one signal a position of said prosthetic device relative to said position of said body component,
        wherein said at least one signal has a substantially time-varying component and a substantially constant value, wherein said processor is configured to detect when said at least one signal exhibits a time-varying component that matches a pattern and determine said position of said body component based on said at least one signal, and
    wherein said processor generates feedback data regarding the positioning of one or more of said body component and said prosthetic device,
        wherein said processor is further configured to detect when said signal exhibits a constant value that exceeds a predetermined threshold value and determine said position of said prosthetic device based on said at least one signal.

2. A method for placing a prosthetic aortic valve comprising the steps of:
    inserting a guide wire through a vasculature of a patient;
    detecting, by at least one sensor disposed on the guide wire, a body component;
    determining, by a processor, a position of the body component based on at least one signal received from the at least one sensor;
    feeding a catheter along the guide wire through the vasculature;
    detecting, by the at least one sensor, a prosthetic aortic valve disposed on at least part of the catheter as the catheter is fed along the guide wire;
    determining, by the processor, a position of the prosthetic aortic valve along the guide wire based on the at least one signal received from the at least one sensor; and
    generating, by the processor, feedback information indicating the position of the prosthetic aortic valve relative to the position of the body component.

3. The method of claim 2, wherein said first determining step further comprises the step of detecting, by the processor, a signal indicating a periodic contact with the at least one sensor indicating a heart beating and the body component opening and closing with the heart beat.

4. The method of claim 3, wherein said first determining step further comprises the step of determining, by the processor, a position of a coaptation point of the body component by determining which at least one sensor that receives the periodic contact is most proximal along the guide wire to a user interface box housing the processor.

5. The method of claim 2, wherein said second determining step further comprises the step of determining, by the processor, a position of an annulus of the prosthetic device by referencing catheter and prosthetic device dimensional data.

6. The method of claim 2, wherein the body component is an aortic valve.

7. The method of claim 2, wherein the at least one sensor comprises one or more of at least one poly-vinylidene fluoride piezoelectric contact sensor, at least one microelectromechanical system sensor, and at least one strain sensor.

* * * * *